(12) United States Patent
Dietrich et al.

(10) Patent No.: US 12,042,198 B2
(45) Date of Patent: Jul. 23, 2024

(54) SURGICAL SCREW SYSTEM FOR INJURIES OF THE PELVIS

(71) Applicant: Dieter Marquardt Medizintechnik GmbH, Spaichingen (DE)

(72) Inventors: Timo Dietrich, Spaichingen (DE); Akhil P. Verheyden, Freiburg (DE)

(73) Assignee: DIETER MARQUARDT MEDIZINTECHNIK GMBH, Spaichingen (DE)

( * ) Notice: Subject to any disclaimer, the term of this patent is extended or adjusted under 35 U.S.C. 154(b) by 307 days.

(21) Appl. No.: 17/512,158

(22) Filed: Oct. 27, 2021

(65) Prior Publication Data
US 2022/0125497 A1   Apr. 28, 2022

(30) Foreign Application Priority Data
Oct. 27, 2020   (DE) ...................... 10 2020 128 211.7

(51) Int. Cl.
*A61B 17/88*   (2006.01)
*A61B 17/86*   (2006.01)

(52) U.S. Cl.
CPC ...... *A61B 17/8888* (2013.01); *A61B 17/8605* (2013.01); *A61B 17/864* (2013.01); *A61B 17/8665* (2013.01); *A61B 17/8695* (2013.01)

(58) Field of Classification Search
CPC ............ A61B 17/8665; A61B 17/8695; A61B 17/8888
See application file for complete search history.

(56) References Cited

U.S. PATENT DOCUMENTS

| | | |
|---|---|---|
| 4,433,677 A | 2/1984 | Ulrich et al. |
| 6,635,059 B2 | 10/2003 | Randall et al. |
| 9,517,095 B2 | 12/2016 | Vaidya |
| 9,662,158 B2 | 5/2017 | Reiley |
| 9,949,843 B2 | 4/2018 | Reiley et al. |
| 2009/0192551 A1 | 7/2009 | Cianfrani et al. |
| 2015/0112444 A1 | 4/2015 | Aksu |
| 2015/0320450 A1 | 11/2015 | Mootien et al. |

(Continued)

FOREIGN PATENT DOCUMENTS

| | | |
|---|---|---|
| CN | 203074841 U | 7/2013 |
| DE | 102017005222 A1 | 12/2018 |

(Continued)

OTHER PUBLICATIONS

German Search Report issued Jun. 2, 2021 in connection with corresponding German Patent Application No. search report DE 10 2020 128 211.7.

(Continued)

*Primary Examiner* — Olivia C Chang
(74) *Attorney, Agent, or Firm* — AIRD & MCBURNEY LP (57) ABSTRACT

The present invention relates to a surgical screw connection system (100) for use in the region of the pelvic bone. The surgical screw connection system (100) comprises or consists of at least one rod (10) with a first end section (11) and a second end section (13). The rod (10) is cannulated throughout and the first end section (11) consists of or comprises a first threaded section (111). The present invention also relates to an instrument set (200), a treatment set and a method for securing a locking nut (21).

13 Claims, 6 Drawing Sheets

(56) References Cited

U.S. PATENT DOCUMENTS

| | | | |
|---|---|---|---|
| 2015/0359573 A1* | 12/2015 | Adams | A61B 17/809 |
| | | | 606/319 |
| 2016/0135861 A1* | 5/2016 | Kollmer | A61B 50/20 |
| | | | 606/324 |
| 2016/0157897 A1 | 6/2016 | Vaidya | |
| 2016/0302941 A1 | 10/2016 | Reiley et al. | |
| 2018/0049789 A1 | 2/2018 | Fantigrossi et al. | |
| 2019/0117273 A1 | 4/2019 | Schell et al. | |
| 2019/0262042 A1 | 8/2019 | Mari et al. | |
| 2020/0146721 A1 | 5/2020 | Sadiq | |

FOREIGN PATENT DOCUMENTS

| | | |
|---|---|---|
| WO | 2017/127235 A1 | 7/2017 |
| WO | 2018/219376 A1 | 12/2018 |
| WO | 2019192932 A1 | 10/2019 |

OTHER PUBLICATIONS

English translation of German Search Report issued Jun. 2, 2021 in connection with corresponding German Patent Application No. search report DE 10 2020 128 211.7.
English translation of CN203074841U.
English translation of DE102017005222A1.
English translation of WO2019192932A1.
English Translation of WO2018/219376 from Google Translate dated Jun. 12, 2022.

* cited by examiner

SURGICAL SCREW SYSTEM FOR INJURIES OF THE PELVIS

The present invention relates to a surgical screw system according to claim 1, an instrument set according to claim 16, also a treatment set according to claim 20 and a method according to claim 21 or according to each of the preambles or generic terms of these claims.

If fractures of or to the sacrum or dislocations of the sacroiliac joint have to be treated in region of the pelvic bone requiring fixation of the posterior pelvis, screw connection systems are used.

It is an object of the present invention to specify a further surgical screw connection system, an instrument set intended for use therewith, as well as a treatment set and a method for securing the surgical screw connection system.

The object according to the present invention is achieved by a surgical screw connection system with the features of claim 1 and by an instrument set with the features of claim 16. In addition, it is achieved by a treatment set with the features of claim 20 and by the method with the features of claim 21.

The present invention relates to a surgical screw connection system (hereinafter also referred to as screw system for short) for use in the region of the pelvic bone, in particular in the case of fractures of or at the sacrum or dislocations of the sacroiliac joint requiring a fixation of the posterior pelvis.

The screw system according to the present invention comprises at least one rod for use in the pelvic region with a first end section and a second end section, or consists of this rod. The rod is continuously cannulated, that is to say along its entire longitudinal extension. Its first end section comprises or consists of a first threaded section.

A cannulation can in principle be understood here as a longitudinal channel.

The present invention further relates to an instrument set. It encompasses or consists of instruments for the minimally invasive introduction of a surgical screw system for use in the region of the pelvic bone, especially in the case of fractures of or at the sacrum, dislocations of the sacroiliac joint requiring fixation of the posterior pelvis, in particular a screw system according to the present invention, alternatively a rod of that screw system.

The instrument set according to the present invention comprises a first cannulated rotary tool for turning or screwing the compression nut of the surgical screw system. The cannulation, which usually results in or is a lumen running in the longitudinal direction of the object in question, is dimensioned both in diameter and in length in order to accommodate a second rotary tool for turning or screwing the locking nut.

The present invention further relates to a treatment set, having a surgical screw connection system according to the present invention and an instrument set according to the present invention.

The method according to the present invention serves to secure a compression nut which is or will be placed on a first end section of a minimally invasive inserted rod of a surgical screw system according to the present invention and is fixed using a locking nut.

The method encompasses the step of placing the first cannulated rotary tool of the instrument set according to the present invention on the compression nut, alternatively holding the already placed rotary tool, if it is already placed on the compression nut, in its placed position.

The method further comprises holding the compression nut via the first cannulated rotary tool in its initial rotary position or initial angular position, alternatively further tightening the same in a first rotational direction.

Furthermore, the method includes as a further step placing the second rotary tool of the instrument set according to the present invention on the locking nut, wherein or whilst this is positioned on the rod or on the compression nut by inserting the second rotary tool through the cannulation of the first rotary tool, or wherein this has already been positioned on the rod or screwed against the compression nut.

Additionally, encompassed as a further step of the method according to the present invention, is turning or screwing the locking nut using the second rotary tool in a rotational direction opposite to the first rotational direction against the first rotary tool by countering, or for countering, the compression nut.

All of the advantages that can be achieved with the method according to the present invention can also be achieved undiminished in certain embodiments according to the present invention with the apparatuses according to the present invention, and vice versa.

Embodiments according to the invention can have some, several or all of the following features in any combination, unless this is recognized as technically impossible for the person skilled in the art. Advantageous developments of the present invention are each also subject-matter of the sub-claims and embodiments.

In all of the statements made herein, the use of the expression "may be" or "may have" and so on, is to be understood synonymously with "preferably is" or "preferably has," and so on respectively, and is intended to illustrate embodiments according to the present invention.

Whenever numerical words are mentioned herein, the person skilled in the art shall recognize or understand them as indications of a numerical lower limit. Unless it leads the person skilled in the art to an evident contradiction, the person skilled in the art shall comprehend the specification for example of "one" (also "a/an") as encompassing "at least one". This understanding is also equally encompassed by the present invention as the interpretation that a numeric word, for example, "one" (also "a/an") may alternatively mean "exactly one", wherever this is evidently technically possible for the person skilled in the art. Both understandings are encompassed by the present invention and apply herein to all used numerical words.

When an embodiment is mentioned herein, it represents an exemplary embodiment according to the present invention.

When it is disclosed herein that the subject-matter according to the present invention comprises one or several features in a certain embodiment, it is also respectively disclosed herein that the subject-matter according to the present invention does, in other embodiments, likewise according to the present invention, explicitly not comprise this or these features, for example, in the sense of a disclaimer. Therefore, for every embodiment mentioned herein it applies that the converse embodiment, e.g. formulated as negation, is also disclosed.

Embodiments according to the present invention can have one, several or all of the features mentioned above and/or in the following in any technically possible combination.

In several embodiments of the screw system according to the present invention, the first threaded section is or comprises a metric, preferably two-start or multiple-start thread.

In an exemplary embodiment, the metric thread comprises, for example, a cutting edge and is therefore preferably self-tapping.

In some embodiments, the second end section consists of or comprises a second threaded section. The second threaded section can be an internal thread or preferably an external thread.

In several embodiments, the second threaded section is preferably an external thread, for example a self-tapping bone thread and/or a cortical thread, or comprises such a thread.

In some embodiments of the screw system, the rod comprises an intermediate section between the first end section and the second end section which is not threaded on its outside. The outer diameter of the intermediate section is preferably, for example 0.25 times, smaller than the outer diameter of the second thread.

In several embodiments, the screw system also comprises at least one locking nut, preferably with an internal thread. This can be used to block or counter the compression nut. Thereby, it can limit the rod its end side or form its end.

In some embodiments, the screw system further comprises a first washer.

In several embodiments, the screw system further comprises at least one compression nut. The compression nut can be provided to tighten the rod at the end against the bony structures of the pelvis, or to contribute to this.

In some embodiments, the compression nut and the first washer are movably connected to one another via a hinge section. The connection can be permanent. It can be such that it cannot be released without it causing damage.

In several embodiments, the compression nut comprises a larger outside diameter than the locking nut. In other embodiments this is not the case or vice versa.

In some embodiments, the screw system further includes a second washer. The second washer can be provided to tighten the rod against the bony structures of the pelvis, or to contribute to this.

In some embodiments, the first washer and/or the second washer are each placed or can be placed on the rod so as to be movable relative to the first or second end section, respectively.

In some embodiments, the second washer is arranged so as to be movable in an axial direction between the second threaded section and a head section of the second end section or of the rod. Thereby, it can be limited by the second threaded section and the head section in the axial direction of the rod.

Alternatively or additionally, the second washer can be limited in a form-fitting manner in an axial direction by the second threaded section on the one hand and the head section on the other.

The first and/or second washer may each have a through opening for the rod to pass through them, the through opening having a diameter, dimension or opening area which is at least 125% of the corresponding value of the rod at the point where the washer is placed on the rod in order to remain there.

This ensures that the washer, once mounted, is axially fixed to the head section of the rod but can still rotate and remain angularly movable.

First and/or second washer may each have a through opening having a diameter associated with the centre of the rod which is less than a diameter associated with the end of the rod.

The first and/or second washer are preferably configured to be able to assume an angle relative to the longitudinal axis of the rod outside a range extending between 75 and 105°.

Preferably, the first and/or second washer are designed in such a way so they can assume an angle of at least 20° relative to the perpendicular to the longitudinal axis of the rod.

In several embodiments, the second end section comprises a front-end engagement opening or a drive. This is used to engage with the tip or the end section of a rotary tool, e.g. the blade of a screwdriver (slot, Allen, polygon such as square or hexagon, Phillips, Torx, etc.).

In some embodiments, the screw system according to the present invention comprises a plurality of rods (at least two), of which at least two or more have different lengths, the difference in length between the individual rods preferably being 5 mm. The shortest rod can preferably be 150 mm or less, the longest preferably 250 mm or more. However, other lengths are also encompassed by the present invention. The rods can each comprise washers, compression nuts, and/or locking nuts.

In several embodiments, the instrument set according to the present invention furthermore comprises a second, preferably cannulated, rotary tool for turning or screwing the locking nut. The second rotary tool is preferably long enough to, once inserted into the first rotary tool, reach at least into an end region of the cannulation.

In several embodiments, the instrument set also comprises an instrument for determining length which carries markings that facilitate selecting the rod that is most suitable for the respective application from the rods contained in the screw system by marking length ranges for the proposed use, e.g. a rod of a first length or a rod of a second length.

If, for example, the surgeon measures the distance to the opposite corticalis using the instrument for determining length along the guide wire, he can easily and directly read the preferred length of the rod recommended for treatment from the instrument for determining length. For this purpose, the instrument for determining length can be cannulated in whole or in part. Alternatively, it can have a longitudinal groove.

It is also encompassed within the present invention that the instrument for determining length additionally or alternatively comprises other markings, for example common length units, e.g. a scale in centimeters or inches.

In some embodiments, the instrument set also comprises at least one Kirschner wire. The length and diameter of the Kirschner wire can be tailored to its use in the pelvic region, for example during an operation. For example, it can have a length of 300 mm and a diameter of 2.8 mm.

In some embodiments, the instrument set also comprises a twist drill. This is preferably cannulated.

In some embodiments, the instrument set additionally comprises an exchange sleeve.

In several embodiments, the method steps can be processed consecutively, overlapping or simultaneously, in certain embodiments partly one after the other, partly overlapping and partly simultaneously.

In several embodiments, the screw system according to the present invention, the instrument set according to the present invention and/or the treatment set according to the present invention is sterile.

In some embodiments, the surgical screw system preferably does not comprise an element which is intended to remain permanently, wholly or partially, in the continuous cannulation of the rod, or to be screwed into it.

In several embodiments, one or more of the elements of the screwing system comprises or consists of Ti-6Al-4V (or Ti64).

In some embodiments, the diameter of the at least one rod is between 5 mm and 10 mm, preferably 7.5 mm, the length is between 120 mm and 250 mm, less than 120 mm or more than 250 mm.

In some embodiments, the screw system or the rod does not comprise a sleeve, a sleeve with a head or with a lens head.

In several embodiments, the rod has no holes in the transverse direction of the rod and/or no radially protruding fins.

In some embodiments, the rod has a metric external thread on both sides, as well as a compression screw and a locking screw on both sides.

In several embodiments, the through opening of the first washer and/or of the second washer comprises a diameter facing its top surface that is smaller than a diameter which is facing its bottom surface.

In some embodiments, the through opening of the first washer and/or of the second washer comprises a diameter that is smaller than a maximum diameter of the head section of the rod or a joint section of the compression nut inserted into the washer.

In this way, the first and/or second washer can be made to be held to the compression nut or to the head section of the rod, but can still rotate and tilt at an angle to the rod or to the longitudinal direction of the compression nut.

In some embodiments, the underside of the first and/or second washer is planar.

In several embodiments, the underside of the first washer and/or of the second washer is not tilted towards each other in at least two planes.

In some embodiments, the rod is not intended to be inserted into a sleeve or another component which would cover the majority of its extension and which has a larger diameter than the rod, or such a component is not part of the screw system.

In several embodiments, the rod is not a two-part element, the two parts of which are interlocked to make the rod telescopic.

In some embodiments, the rod does not have a nut and/or a thread for a nut on its head section.

Several or all embodiments according to the present invention may have one, more or all of the advantages mentioned above and/or below.

If screw systems are used for fixation in the region of the pelvic bone, particularly in the case of fractures on the sacrum or at the sacrum or dislocations of the sacroiliac joint requiring fixation of the posterior pelvis, these screw systems contain solid metal rods which must be shortened to the appropriate length using a bolt cutter. This procedure makes minimally invasive surgery at this point impossible. According to the present invention, this is advantageously different: there is no need for such a shortening, which allows the subject-matters according to the present invention to be used for minimally invasive care.

Due to their mobility relative to the rod, which also includes tilting relative to the rod, the movably arranged washers allow an even distribution of force on the bone.

The provision of rods of different lengths for selection by the surgeon advantageously also allows an intraoperative definition of the optimal end length without the implant or the rod having to be shortened intraoperatively. This opens up the possibility of minimally invasive interventions by using one of the systems according to the present invention, in particular the screw system.

The intermediate section, which optionally has no thread, can contribute to increasing the strength or fatigue strength.

The optional cortical thread can contribute to an increased hold of the implant.

The movably arranged or specially prepared washers can provide an increased actual contact surface and thus ensure a more even distribution of force around the bore through the pelvis. This contributes advantageously to the secure fit of the implant.

Another advantage can be that the washers provide or facilitate safe removal. With conventional washers on the market, which are loosely placed under the screw head without being connected to the associated screw, it can happen that the washer grows together with the bone or tissue. When explanting the rod together with the screw to be loosened for this purpose, it often happens that the screw is removed, but the washer remains in place and consequently has to be explanted with tweezers or the like. When using the present invention, because of the firm connection between the washer and the rod, the washer is advantageously automatically forcibly removed together with the rod or with the compression nut.

Figure 1:
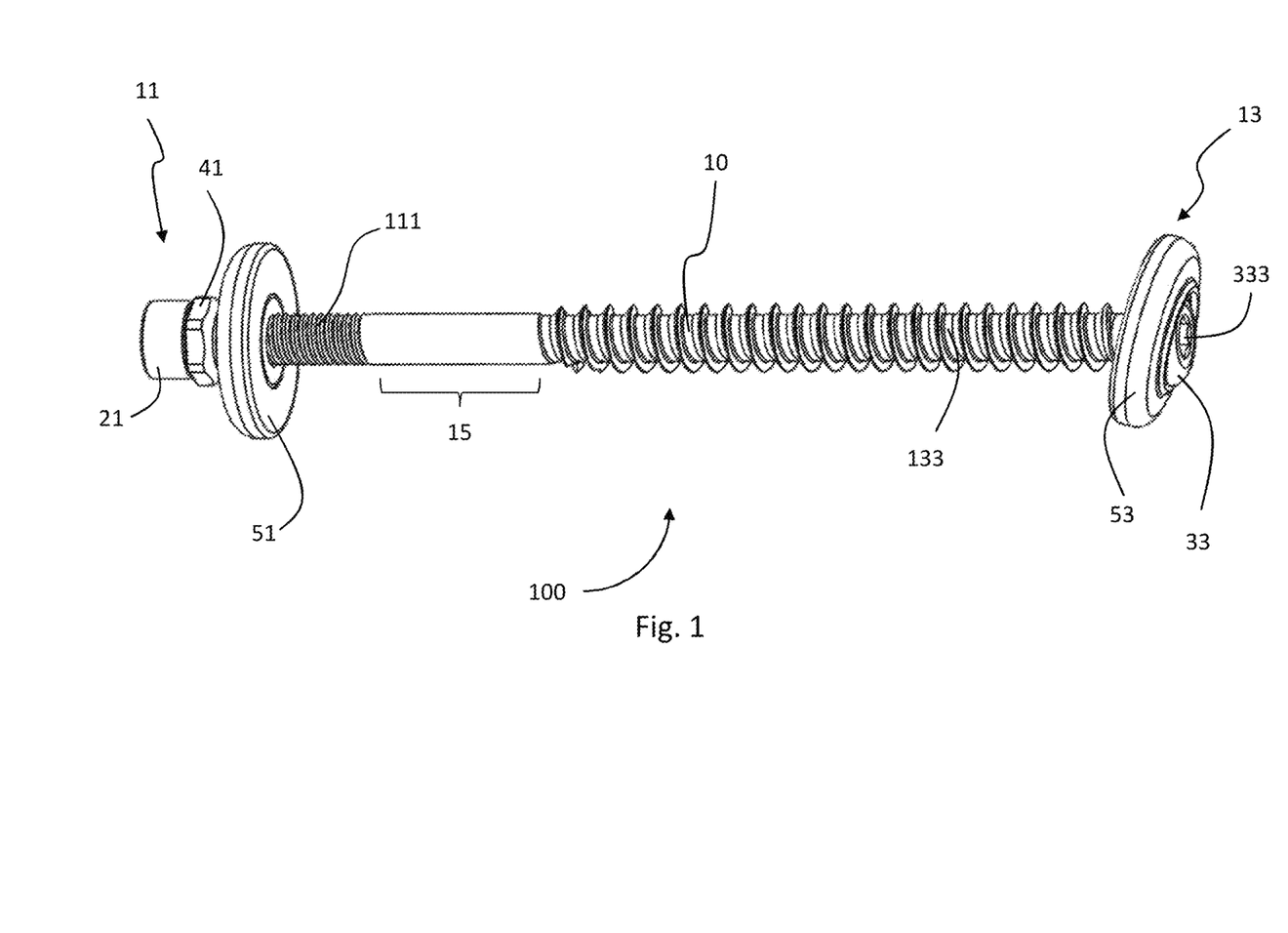
FIG. 1 shows a surgical screw connection system in a first embodiment with a first rod.

The present invention is exemplarily explained with regard to the accompanying drawings in which same reference numerals refer to the same or similar components. In the figures the following applies:

FIG. 1 shows a surgical screw connection system 100 (hereinafter for short: screw system) in a first embodiment for use in the region of the pelvic bone in a perspective view. It can be used in particular on the sacrum or for fractures of the sacrum or for dislocations of the sacroiliac joint with fixation of the posterior pelvis.

The screw system 100 comprises or consists of at least one rod 10 with a first end section 11 and a second end section 13. The rod 10 is cannulated throughout, i.e. along its entire longitudinal section. The cannulation allows the screw system 100 to be advanced minimally invasively, i.e. with no or extremely limited visual control by the surgeon, along a previously inserted Kirschner wire and guided by this through tissue and through bone structures (here in particular the pelvis, sacrum).

The first end section 11 for its part has or comprises a first threaded section 111. The first threaded section 111 can be designed as an internal thread or, as in FIG. 1, as an external thread. The view of the first threaded section 111 is largely obscured in FIG. 1 by an optional, first washer 51 and a compression nut 41, which, like the first washer 51, can be part of the screw system 100.

Compression nut 41 and washer 51 are both assigned to first end section 11 and can in particular be provided to close off rod 10 or the screw system at the end. The first thread section 111 comprises a metric, preferably double-start or multi-start, thread or consists of such. The mostly metric thread comprises, for example, a cutting edge and is therefore preferably self-tapping.

The compression nut 41 can be movably connected to the washer 51, in particular in an articulated manner.

The second end section 13 consists of or comprises an optionally second threaded section 133. The second threaded section 133 can be, preferably as an external thread, a cortical thread and/or self-tapping bone thread or comprise such a thread.

Between the first end section 11 and the second end section 13, the rod 10 comprises an intermediate section 15, which preferably has no thread on its outside, and the outside diameter of which is preferably smaller than the outside diameter of the second threaded section 133.

On the first end section 11, the screw system 100 also comprises an optional locking nut 21. This is provided in order to brace the rod 10 or the screw system 100. For this purpose, it may comprise an internal thread 23 (see FIG. 1c). Furthermore, it can be provided to close off the end section at its end, i.e. to form its end.

In certain embodiments of the screwing system 100, the compression nut 41 and the first washer 51 are connected to a joint section which connects them movably to one another. Optionally, they are unreleasably connected to one another, in any case, preferably without having to cause any damage.

It can be clearly seen in the example in FIG. 1 that the compression nut 41 comprises a larger outer diameter than the locking nut 21. This can also be different or vice versa in some embodiments.

In some embodiments, such as that shown in FIG. 1, the screw system 100 according to the present invention also comprises a second washer 53. This can be assigned to the second end section 13 and be provided in order to close off the rod 10 or the screw system 100 at the end.

The second washer 53 can have a through opening for the second end section 13, which comprises a diameter, a dimension or an opening area which is at least 125% of the corresponding value of the rod at the point at which the washer is placed on the rod in order to remain there.

The second washer 53 is movably arranged in an axial direction between the second threaded section 133 and a head section 33 of the second end section 13. Here, their freedom of movement in the axial direction is limited by the second threaded section 133 and the head section 33 of the rod 10 and/or in a form-fitting manner by the second threaded section 133 on the one hand and the head section 33 on the other hand. During the production of the rod 10 after the second washer 53 has been threaded onto the rod 10, the head section 33 may have been reshaped by compressing the second end section 13 into a diameter which prevents the second washer 53 from slipping down the rod 10.

The second end section 13 preferably comprises a front-end engagement opening 333 (or drive) for engaging with the tip of a rotary tool, for example the end of a screwdriver.

Figure 2:
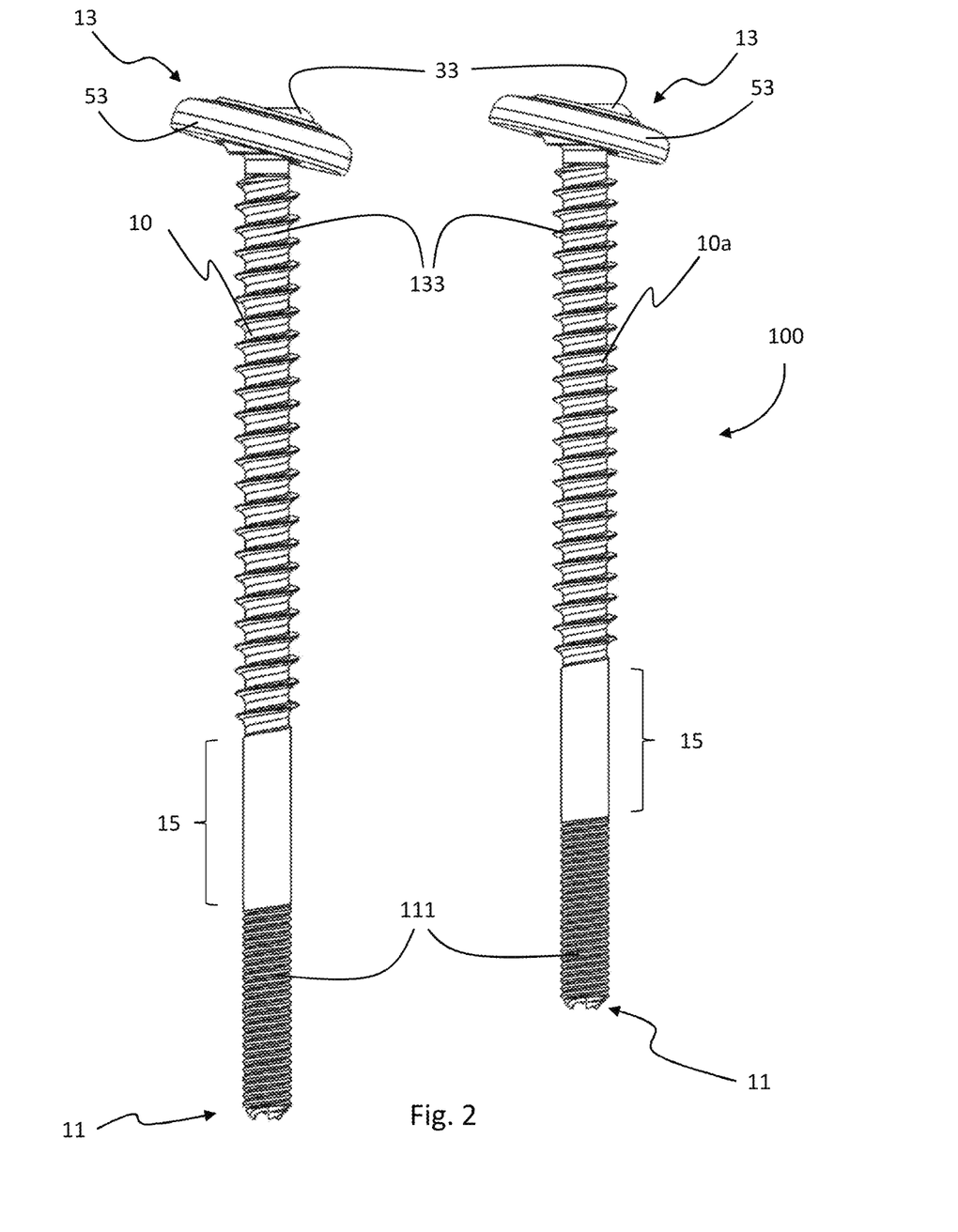
FIG. 2 shows the first rod and a second rod of the surgical screw connection system in a further embodiment having different lengths.

The screw system 100 can comprise a plurality of, at least, two rods 10, 10a configured according to the example in FIG. 1 in different lengths (see FIG. 2).

It may be provided in accordance with the present invention to identify the second washer 53 or other section of the rod 10, 10a with the length of the corresponding rod.

Figures 1A, 1B, 1C:
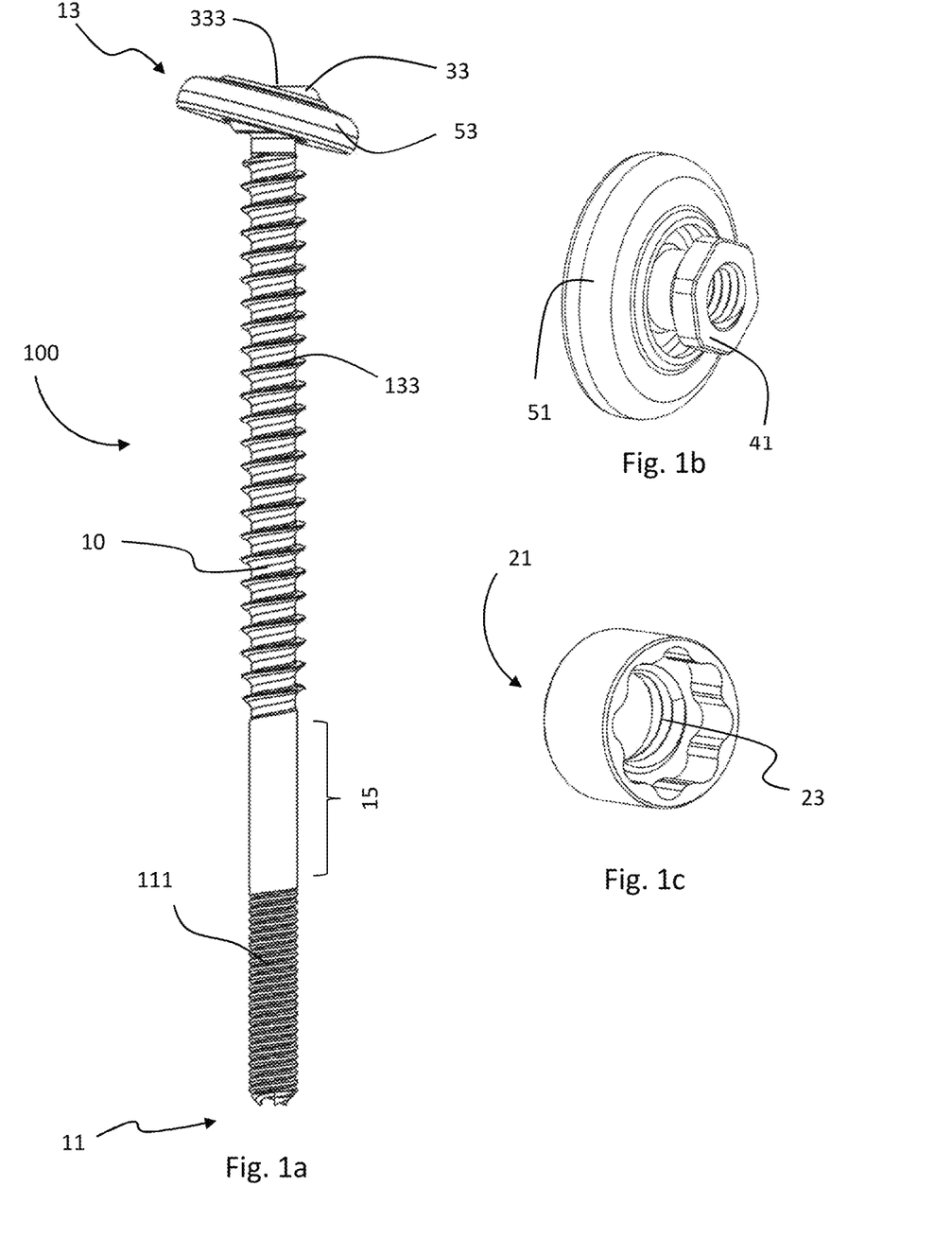
FIG. 1a shows the first rod of FIG. 1 without the compression nut or locking nut.
FIG. 1b shows in an enlarged, slight perspective representation from the side the compression nut and the first washer of FIG. 1
FIG. 1c shows in an enlarged, slight perspective representation from the side, the locking nut of FIG. 1.

FIG. 1a shows the first rod 10 of FIG. 1 without compression nut 41 and without locking nut 21. To avoid repetition, reference is made to the description of FIG. 1.

FIG. 1b shows an enlarged, slightly perspective representation of the compression nut 41 and the first washer 51 of FIG. 1.

The same component can be used as washer 51, 53 for both the rod 10 and the compression nut 41.

FIG. 1c shows an enlarged, slight perspective representation of the locking nut 21 of FIG. 1.

The internal thread 23 of the locking nut 21 can be clearly seen in FIG. 1c. This is used to screw the locking nut 21 to the first threaded section 111 in order to securely fix the compression nut 41 and thus the rod 10, 10a to or in the pelvis.

Figure 3A:
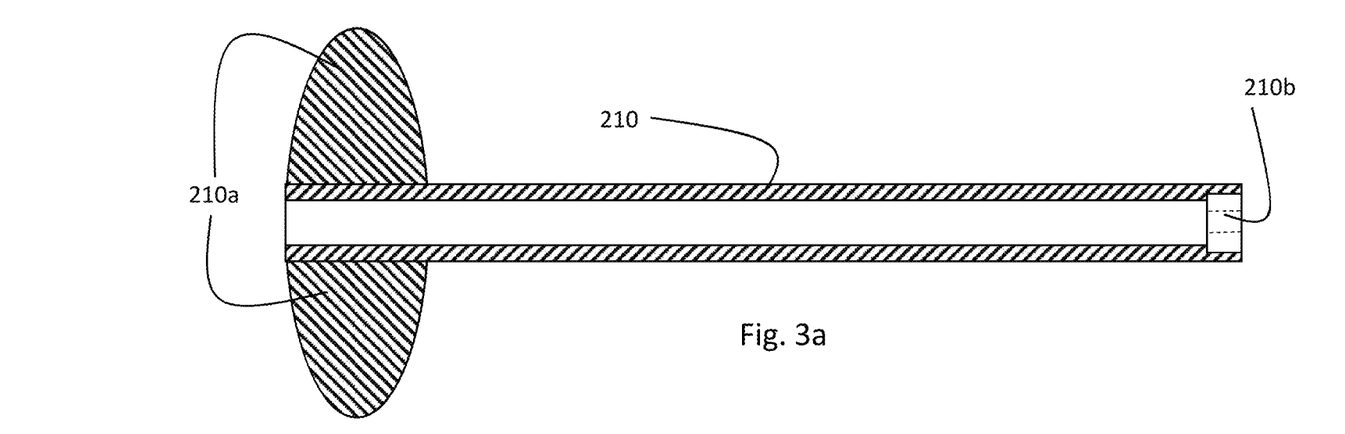
FIGS. 3a to 3c show an instrument set according to the present invention in a first embodiment.
Figures 3B, 3C:
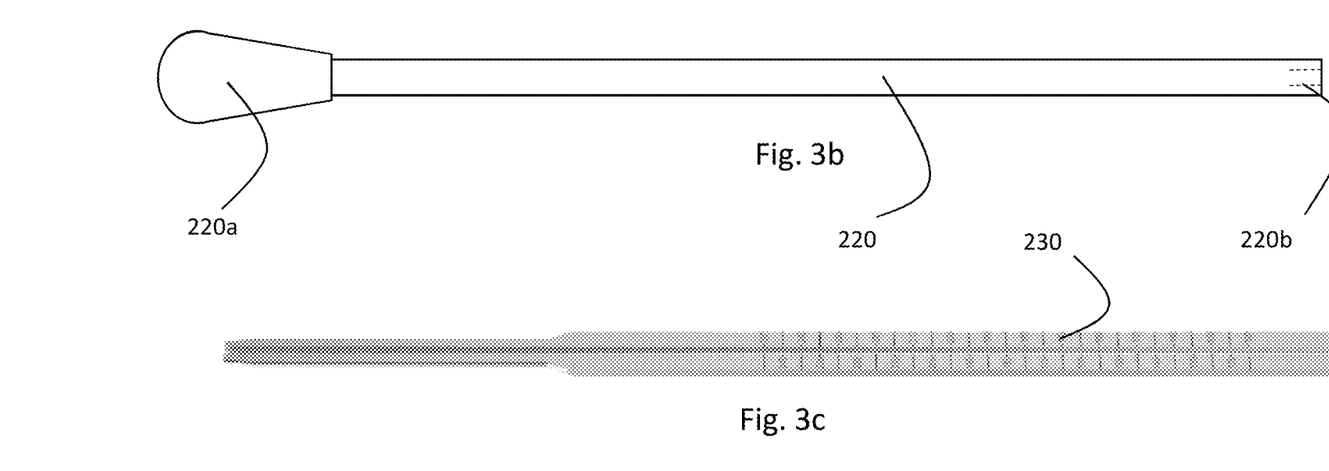

An engagement or drive for placing the rotary tool 220 on the front-end, see exemplary FIG. 3b, can be seen. The locking nut 21 may comprise a Torx engagement or other engagement, in particular for receiving the end section of a rotary tool.

Figure 1D:
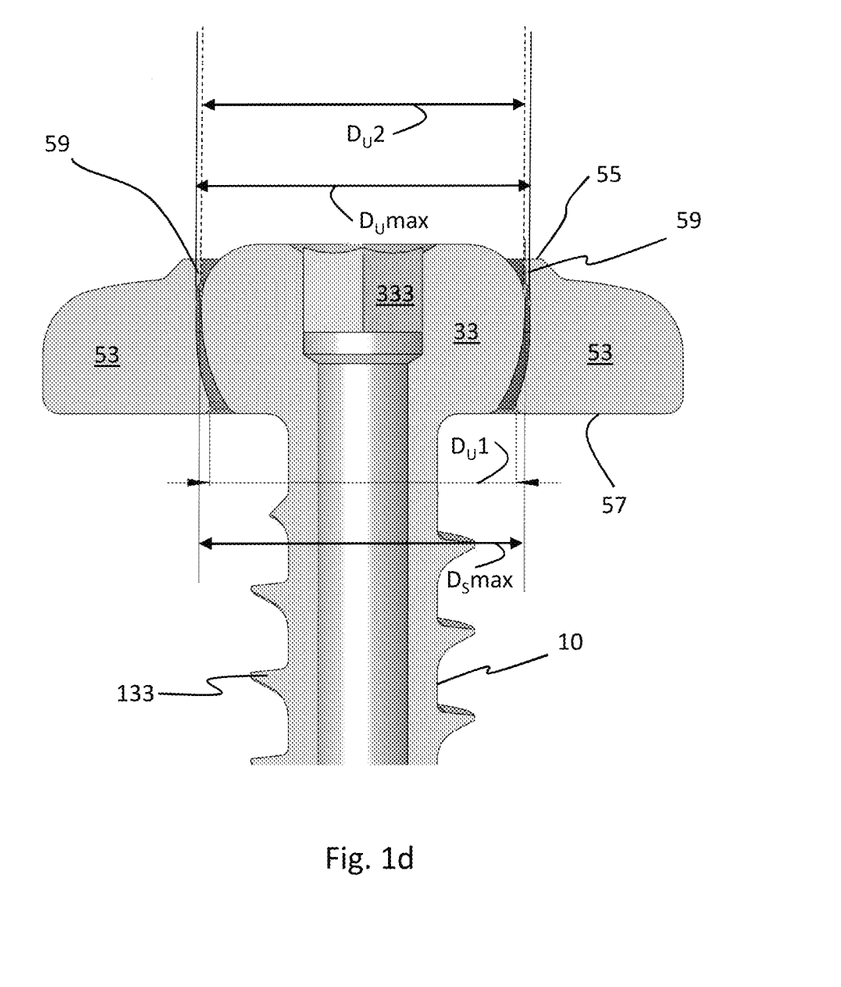
FIG. 1d shows in an enlarged sectional representation the interaction of the head end of a rod of the screw connection system in an embodiment and the washer of this embodiment.

FIG. 1d shows, in an enlarged sectional representation, the interaction between the head section 33 of a rod 10 (shown only in sections) of the surgical screw connection system 100 in an embodiment and the second washer 53 of this embodiment.

The second washer 53 has an upperside 55 and an underside 57. The latter faces the center of the rod 10, and the former faces the end of the rod 10.

The second washer 53 is placed on the head section 33 or the head section 33 is completely or partially inserted into the through opening of the washer 53.

A first diameter $D_U1$ and a second diameter $D_U2$ can be seen in FIG. 1d, wherein the first diameter $D_U1$ is arranged above (with reference to the representation in FIG. 1d) the second diameter $D_U2$.

In the specific example of FIG. 1d it can also be seen that the first diameter $D_U1$ optionally delimits the opening from the underside 57, and that the second diameter $D_U2$ optionally delimits the opening on the upperside 55 or forms its end.

If the first diameter $D_U1$, as in the example in FIG. 1d, is less than the maximum diameter $D_S max$ of the head section 33, the second washer 53 cannot slip over the head section 33 and off the rod 10 (upwards in FIG. 1d).

The changing of a diameter of the washer to the first diameter $D_U1$ required for this may have been created by pressing or some other deformation of the second washer 53 by the manufacturer.

The second diameter $D_U2$ of the through opening may correspond to the maximum diameter $D_U max$ of the through opening, but this is optional.

The washer 53 can optionally have a protrusion 59 or a deformation at the upper end of its through opening, which is suitable for reducing the diameter of the through opening at this end so that $D_U2 < D_U max$ applies. This can prevent the washer 53 from sliding over the head section 33 and possibly off the rod 10 (downwards in FIG. 1d).

What is stated with reference to FIG. 1d for the second washer 53 and the head section 33 can apply analogously to the connection between the first washer 51 and the compression nut 41. They can also be matched to each other by the choice or creation of the diameter ratios described above in such a way that the first washer 51 cannot detach from the compression nut 41, but can still rotate and remain movable in angle, i.e. can tilt.

FIG. 2 shows a second rod 10*a* next to the first rod 10. They differ here in their different lengths.

The design of the rods 10, 10*a* is analogous to FIG. 1, but without the first washer 51, without the compression nut 41 and without the locking nut 21. To avoid repetition, reference is therefore made to the description of FIG. 1.

The screw system 100 may comprise a plurality, at least two, of rods 10, 10*a* of different lengths, the difference in length preferably being 5 mm. In this respect, the shortest rod may preferably be 150 mm, and the longest rod may preferably be 250 mm. However, other lengths are also encompassed by the present invention. The rods may be closed or be able to be closed at each end.

The rods preferably have a diameter of 7.5 mm. Larger or smaller diameters are also encompassed within the present invention.

FIG. 3*a* shows a first rotary tool 210 as part of the instrument set according to the present invention in an embodiment.

The first rotary tool 210 is designed or dimensioned, in particular cannulated, to receive a second rotary tool 220 (see FIG. 3*b*), preferably within its entire length. Furthermore, it is designed to be able to screw in or unscrew or tighten or loosen the compression nut 41 via its blade end 210*b*.

At the end of the first rotary tool 210 opposite the blade end 210*b*, a handle section 210*a* for holding or gripping the rotary tool 210 is provided.

FIG. 3*b* shows a second rotary tool 220 as component of the instrument set according to the present invention in an embodiment in a sectional representation.

The second rotary tool 220 is designed or dimensioned to be able to be inserted into a first rotary tool 210 (see FIG. 3*a*) and to be able to screw in or unscrew or tighten or loosen the locking nut 21 via its blade end 220*b*. It is of corresponding length.

The second rotary tool can preferably be cannulated.

At that end of the second rotary tool 220 opposite the blade end 220*b*, a handle section 220*a* is provided, which in turn serves to make it easier to grip, hold or mechanically operate the rotary tool 200*a*, or to make this possible.

FIG. 3*c* shows an instrument for determining length 230 as an optional component of an instrument set according to the present invention.

The instrument for determining length 230 comprises markings or a scale along its longitudinal section. In some embodiments, the markings or the scale can correspond to the lengths of the rods 10, 10*a* contained in the screw system 100. In use, the instrument for determining length 230 can advantageously specify or indicate the length of a rod 10, 10*a* that is to be preferred, to be used, in particular to be inserted, in the sense of a suggestion addressed to the surgeon.

In certain embodiments, the instrument set 200 further comprises at least one Kirschner wire (not shown in the figures), matched in length and diameter to the dimensions in the field of application of the present invention, preferably having a diameter of 2.8 mm and a length of e.g. 300 mm.

Figure 4:
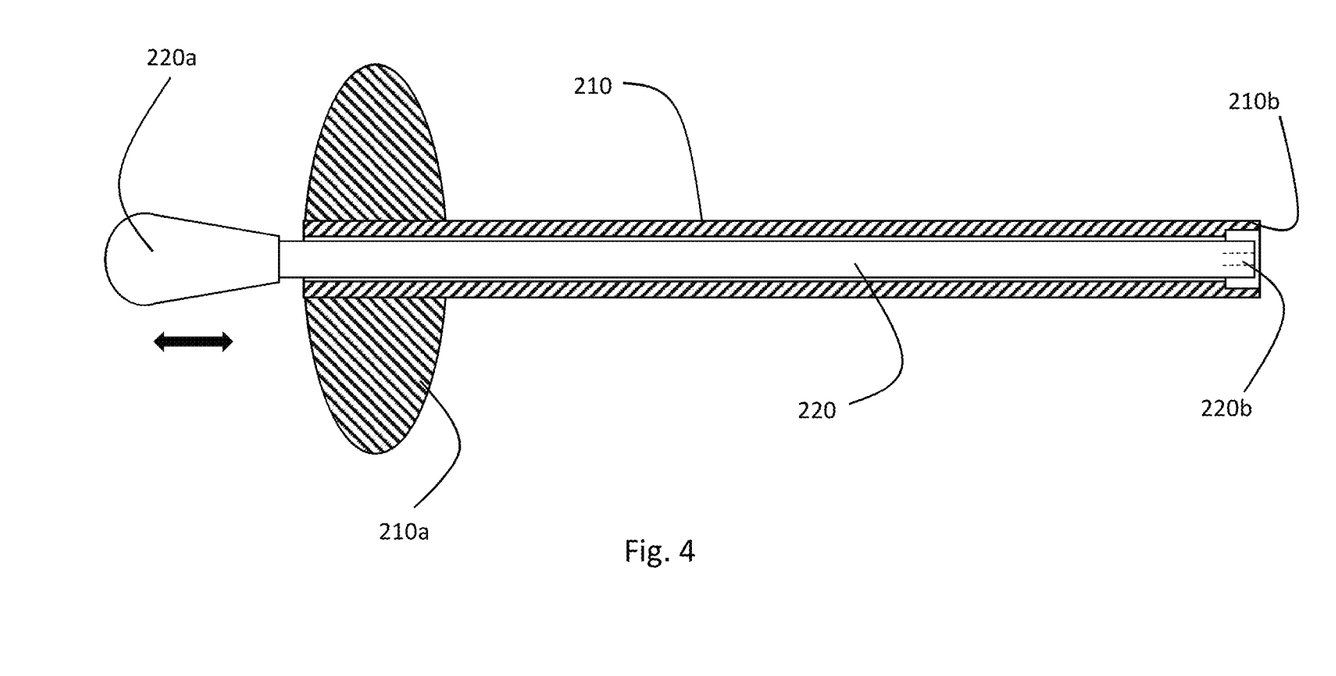
FIG. 4 shows a first rotary tool of the instrument set of FIG. 3, in which a second rotary tool of the instrument set is inserted.

FIG. 4 shows the first rotary tool 210 of the instrument set according to the present invention of FIG. 3 with the second rotary tool 220 of the instrument set inserted.

The cannulated first rotary tool 210 for the compression nut 41 is dimensioned both in diameter and length such that it can receive the second rotary tool 220 for the locking nut 21 in its cannulation, at least up to an end region of the cannulation. This is indicated in FIG. 4 via a double arrow.

In particular, the first rotary tool 210 is configured to retain the compression nut 41 and thus prevent it from rotating with the locking nut 21 when the locking nut 21 is tightened or loosened by the second rotary tool 220.

A typical application of the present invention may be as follows:

Access is made through a stab incision over the planned rod entry site on the sacral bone (also: sacrum, level of vertebral body S1).

The first sacral vertebral body S1 is located with the aid of an image converter.

The Kirschner wire is inserted in the lateral beam/ray path up to the opposite cortical bone according to the anatomical conditions.

This is followed by inlet and outlet images and, if necessary, a correction of the wire's position.

The correct position of the Kirschner wire is preferably verified via a 3D scan. The Kirschner wire should run at an angle of approx. 90° to the fracture gap. Alternatively, the Kirschner wire can be inserted using 3D navigation.

Using a cannulated twist drill, which may be part of the instrument set 200 according to the present invention, the cortical bone is drilled via the Kirschner wire through the drill sleeve. The Kirschner wire must be completely overdrilled. The over-drilled Kirschner wire is then removed.

The guide wire (e.g. length 520 mm) is now pushed through the cannulated twist drill which remained in the body. A replacement sleeve, which may also be part of the instrument set 200 according to the present invention, is advanced over the guide wire as far as it will go. The guide wire must be flush with the replacement sleeve.

The instrument for determining length 230 is then introduced over the guide wire to the opposite cortical bone. For this purpose, it can be wholly or partially cannulated. It can have a longitudinal groove.

The required rod length can be read directly from the scale of the instrument for determining length 230.

The instrument for determining length 230 is preferably open on one long side so that the upper part, but less than the full circumference, of the guide wire remains visible in order to be able to compare the end of the guide wire with the scale on the instrument for determining length 230. If the rod length determined in this way lies between two scale values, the longer rod length is preferably selected. The scale thus indicates rod lengths, which is not done in cm or inches, but in allocations to available rods.

The rod 10 of the screw system 100 according to the present invention is introduced over the guide wire with a cannulated rotary tool, such as a screwdriver.

The rod 10 most be screwed in until the washer 53 of the second end section 13 rests against the bone.

From the opposite side, using the first rotary tool 210, the compression nut 41 with washer 51 is screwed over the guide wire onto the first end section 11 of the rod 10 and the desired compression is set.

Finally, the second rotary tool 220 is used to insert the locking nut 21 through the first rotary tool 210. The distal end of the second rotary tool 220 reaches the end of the cannulation of the first rotary tool 210. While countering the compression nut 41, e.g. by holding the first rotary tool 210, the locking nut 21 can be hand-tightened using the second rotary tool 220.

LIST OF REFERENCE NUMERALS

100 surgical screw connection system
10 rod 10a rod
11 first end section
13 second end section
15 intermediate section
21 locking nut
23 locking nut internal thread
33 head section
333 engagement opening
41 compression nut
51 first washer
53 second washer
55 upperside of the second washer
57 underside of the second washer
59 protrusion; deformation
111 first threaded section
133 second threaded section
200 instrument set
210 first rotary tool (for compression nut)
210a handle section of first rotary tool
210b blade end of first rotary tool
220 second rotary tool (for locking nut)
220a handle section of second rotary tool
220b blade end of second rotary tool
230 instrument for determining length
$D_U1$ first diameter of through opening of washer (underside)
$D_U2$ second diameter of through opening of washer (upperside)
$D_U$max maximum diameter of through opening of washer
$D_S$max maximum rod diameter (head section)

The invention claimed is:

1. A surgical screw connection system for use in the region of the pelvic bone, comprising or consisting of:
    at least one rod having a first end section and a second end section;
    a first washer; and
    a compression nut;
    wherein the rod is cannulated throughout;
    wherein the first end section comprises or consists of a first threaded section; and
    wherein the compression nut and the first washer are connected by a joint section, which movably connects them to each other.

2. The surgical screw connection system according to claim 1, wherein the first threaded section is or comprises a metric thread, preferably a double thread.

3. The surgical screw connection system according to claim 1, wherein the second end section comprises or consists of a second threaded section.

4. The surgical screw connection system according to claim 3, wherein the second threaded section is or comprises a cortical thread or self-tapping bone thread.

5. The surgical screw connection system according to claim 3, wherein the rod comprises an intermediate section between the first end section and the second end section, which does not have a thread on its outer side and whose outer diameter is preferably smaller than the outer diameter of the second threaded section.

6. The surgical screw connection system according to claim 1, further comprising at least one locking nut.

7. The surgical screw connection system according to claim 6, wherein the compression nut comprises a larger outer diameter than the at least one locking nut.

8. The surgical screw connection system according to claim 1, further comprising a second washer.

9. The surgical screw connection system according to claim 1, wherein the first washer is or can be placed on the first end section, and is movable relative to the rod.

10. The surgical screw connection system) according to claim 1,
    wherein the second end section comprises or consists of a second threaded section,
    wherein the surgical screw connection system further comprises a second washer, and
    wherein the second washer is arranged so as to be movable in an axial direction between the second threaded section and a head section of the second end section, and is limited by the second threaded section and head section in an axial direction of the rod and/or it is limited in an axial direction in a form-fitting manner by the second threaded section on the one hand and the head section on the other.

11. The surgical screw connection system according to claim 1, wherein the second end section comprises a front-end engagement opening for engaging with the tip or the end section of a rotary tool, e.g. of a screw driver.

12. The surgical screw connection system according to claim 1, comprising a plurality, at least two, rods of different lengths, wherein the difference in length is preferably 5 mm.

13. The surgical screw connection system according to claim 8, wherein the second washer is or can be placed on the second end section, and is movable relative to the rod.

* * * * *